US010836660B2

(12) United States Patent
Martin

(10) Patent No.: US 10,836,660 B2
(45) Date of Patent: *Nov. 17, 2020

(54) METHOD AND COMPOSITION FOR USE IN THE CYCLIC PROCESS FOR THE EFFICIENT GENERATION OF CHLORINE DIOXIDE IN DILUTE SOLUTIONS

(71) Applicant: Roy W. Martin, Downers Grove, IL (US)

(72) Inventor: Roy W. Martin, Downers Grove, IL (US)

(73) Assignee: Truox, Inc., Alpine, WY (US)

( * ) Notice: Subject to any disclaimer, the term of this patent is extended or adjusted under 35 U.S.C. 154(b) by 27 days.

This patent is subject to a terminal disclaimer.

(21) Appl. No.: 16/501,533

(22) Filed: Apr. 25, 2019

(65) Prior Publication Data
US 2020/0189944 A1 Jun. 18, 2020

Related U.S. Application Data

(63) Continuation-in-part of application No. 16/350,668, filed on Dec. 18, 2018.

(51) Int. Cl.
C02F 1/00 (2006.01)
C02F 1/76 (2006.01)
G01N 33/18 (2006.01)
C02F 103/42 (2006.01)

(52) U.S. Cl.
CPC .............. *C02F 1/766* (2013.01); *C02F 1/008* (2013.01); *C02F 1/76* (2013.01); *G01N 33/182* (2013.01); *C02F 2103/42* (2013.01); *C02F 2209/29* (2013.01); *C02F 2303/04* (2013.01)

(58) Field of Classification Search
CPC .. C02F 1/76; C02F 1/766; C02F 1/008; C02F 2209/29; C02F 2303/04; C02F 2103/42; G01N 33/182
See application file for complete search history.

(56) References Cited

U.S. PATENT DOCUMENTS

| 5,888,428 A * | 3/1999 | Howarth ................. C02F 1/766 210/753 |
| 6,749,758 B2 | 6/2004 | Sander |
| 7,922,933 B2 | 4/2011 | Martin |
| 7,927,509 B2 | 4/2011 | Martin |
| 7,976,725 B2 | 7/2011 | Martin |
| 2010/0178356 A1 * | 7/2010 | Martin .................... C02F 1/725 424/613 |

* cited by examiner

*Primary Examiner* — Lucas A Stelling

(57) ABSTRACT

This invention relates to a method for monitoring and controlling the relative concentration of bromide ion used in the cyclic process for enhanced sanitation and oxidation of aqueous systems at aquatic facilities.

26 Claims, 4 Drawing Sheets

Bromate Inhibition under UV

| | | 1 | 6 | 10 | 18 | 26 | 29 | 36 | 42 | 50 | 57 | 64 | 71 |
|---|---|---|---|---|---|---|---|---|---|---|---|---|---|
| Pool 1 | day | | | | | | | | | | | | |
| | DMH[a] | 44 | 43 | 37 | 30 | 32 | 29 | 20 | 24 | 17 | 14 | 8 | 0 |
| | bromate | 0 | 0 | 0 | 0 | 0 | 0 | 0 | 0 | 0 | 0 | 1 | 5 |
| | bromide | 50 | 35 | 30 | 31 | 34 | 33 | 33 | 32 | 33 | 29 | 30 | 26 |
| Pool 2 | day | 1 | 6 | 10 | 18 | 26 | 29 | 36 | 42 | 50 | 57 | 64 | 71 |
| | DMH[a] | 33 | 27 | 30 | 29 | 19 | 20 | 14 | 13 | 8 | 3 | 4 | 0 |
| | bromate | 0 | 0 | 0 | 0 | 0 | 0 | 0 | 0 | 0 | 0 | 1 | 7 |
| | bromide | 38 | 20 | 23 | 26 | 29 | 39 | 28 | 36 | 26 | 42 | 27 | 20 |
| Pool 3 | day | 1 | 6 | 10 | 18 | 26 | 29 | 36 | 42 | 50 | 57 n/a | n/a | n/a |
| | DMH[a] | 52 n/a | 43 | 33 | 20 | 23 | 7 | 0 | 4 | 0 n/a | n/a | n/a | |
| | bromate | 0 n/a | 0 | 0 | 0 | 0 | 6 | 5 | 5 | 7 n/a | n/a | n/a | |
| | bromide | 36 n/a | 27 | 34 | 27 | 36 | 20 | 14 | 18 | 15 n/a | n/a | n/a | |

[a]DMH = 5,5-dimethylhydantoin

Figure 2

| Lapsed Time (min) | Br- (ppm) | DPD as Cl₂ | ClO₂ | pH | ORP (mV) |
|---|---|---|---|---|---|
| 10 | 0 | 4.2 | 0.00 | 7.45 | 716 |
| 25 | 5 | n/a | 0.33 | 7.47 | 741 |
| 40 | 10 | 4.2 | 0.43 | 7.46 | 744 |
| 55 | 20 | n/a | 0.45 | 7.40 | 750 |
| 70 | 44 | n/a | 0.52 | 7.43 | 754 |

Figure 3

TABLE 1
SUMMARY OF RESULTS

| Sample ID | Oocysts/Well | Results |
|---|---|---|
| 100276-001 Beaker A; Time = 0 | 10000 | 4/4 + |
| | 1000 | 4/4 + |
| | 100 | 4/4 + |
| 100276-002 Beaker A; Time = 6 hr | 1000 | 4/4 + |
| | 100 | 0/4 + |
| 100276-003 Beaker A; Time = 8 hr | 1000 | 2/4 + |
| | 100 | 0/4 + |
| 100276-004 Beaker A; Time = 10 hr | 1000 | 1/4 + |
| | 100 | 0/4 + |
| 100276-005 Beaker A; Time = 12 hr | 1000 | 0/4 + |
| | 100 | 0/4 + |
| 100276-006 Beaker B; Time = 0 | 10000 | 4/4 + |
| | 1000 | 4/4 + |
| | 100 | 3/4 + |
| 100276-007 Beaker B; Time = 6 hr | 1000 | 0/3 +* |
| | 100 | 0/4 + |
| 100276-008 Beaker B; Time = 8 hr | 10000 | 0/4 + |
| | 1000 | 0/4 + |
| | 100 | 0/4 + |
| 100276-009 Beaker B; Time = 10 hr | 1000 | 0/4 + |
| | 100 | 0/4 + |
| 100276-010 Beaker B; Time = 12 hr | 1000 | 0/4 + |
| | 100 | 0/4 + |

* One well on the slide was cracked and could not be read, therefore there were only 3 wells.

Figure 4

METHOD AND COMPOSITION FOR USE IN THE CYCLIC PROCESS FOR THE EFFICIENT GENERATION OF CHLORINE DIOXIDE IN DILUTE SOLUTIONS

BACKGROUND OF THE INVENTION

Field of Invention

This invention relates to a method for monitoring and controlling the relative concentration of precursor used for sanitation and oxidation of aqueous systems at aquatic facilities.

Background of the Technology

Aqueous systems that are exposed to various forms of oxidant demand as well as introduction of microbiological contamination must be effectively treated to control transfer of disease such as in the case of a swimming pool.

Free Bromine is an effective biocide used to treat aqueous systems. However, while free bromine can be easily tested, the bromide precursor used to produce the free bromine requires expensive laboratory equipment (i.e. ion chromatography).

Chlorine dioxide has been proven very effective at inactivating microbiological organisms in such applications. However, generating chlorine dioxide can be hazardous due to the explosive nature of the gas as well as the potential for human exposure to toxic concentrations. Furthermore chlorite anion concentrations must be held to a minimum in water that may be consumed due to toxicity concerns. The U.S. EPA has put a limit in drinking water at 1.0 ppm as chlorite anion.

Chlorine dioxide is typically produced in a chlorine dioxide generator where either acid &/or chlorine is combined with a chlorite donor to generate chlorine dioxide. In order to achieve efficient conversion of chlorite to chlorine dioxide, high concentrations are reacted thereby generating a high concentration of gas which is potentially hazardous.

Using these methods of chlorine dioxide generation also waste considerable amounts of reagents such as chlorite as well as elevate cost due to the inability to regenerate the chlorite ions that result from the reduction of the chlorine dioxide back to chlorite or the residual chlorite that was not activated during the initial formation of chlorine dioxide.

A cyclic process has been developed that utilizes free bromine at near neutral pH to in-situ generate chlorine dioxide. However, in order to ensure free bromine is available to drive the in-situ generation of chlorine dioxide requires a sufficient reserve of bromide ions in the water.

Regardless of whether the aqueous system being treated is using a bromine based biocide or in-situ generated chlorine dioxide using the cyclic process, the treatment program requires an ability to determine the relative amounts of bromide ions in the water.

A method for determining the relative concentration of bromide ions in the aqueous system is provided to ensure sufficient residual of bromide ions is maintained to provide required free bromine.

Prior Art

U.S. Pat. Nos. 7,922,933, 7,927,509, and 7,976,725 which are herein incorporated by reference, disclose a cyclic process for the in-situ generation of chlorine dioxide. The cyclic process utilizes bromide ions that are activated by an oxidant to produce free bromine. The free bromine oxidizes chlorite ions producing chlorine dioxide. Chlorine dioxide inactivates microbiological organisms (i.e. *Cryptosporidium*). During this process the free bromine and at least some portion of the chlorine dioxide are reduced back to bromide ions and chlorite ions respectively which are recycled back to free bromine and chlorine dioxide utilizing the cyclic process.

U.S. Pat. No. 6,303,038 describes uses a halogenated hydantoin and ORP controller to control the concentration of free bromine using ORP. The bromide ion concentration was measured using ion chromatography.

Discussion of Prior Art

The referenced cyclic process patents demonstrate that free chlorine at near neutral pH does not convert chlorite ions into chlorine dioxide to an acceptable level to be useful in the cyclic process. More specifically, the pH range for aqueous systems at aquatic facilities based on Florida Department of Health guidelines is 7.2 to 7.8. Data from the referenced patents demonstrated that at pH 7.45 and 4.2 ppm free chlorine reported as $Cl_2$, no detectable levels of chlorine dioxide was produced. However, when 5 ppm as bromide ions were added the chlorine dioxide was rapidly produced under the same conditions.

The data demonstrates how crucial the presence of bromide ions is to the successful implementation of the cyclic process and ultimately the microbiological efficacy of the treatment program.

Therefore, it is necessary to be able to determine the relative concentration of bromide ions in the aqueous system of an aquatic facility to ensure the cyclic process and subsequently the microbiological efficacy is achieved.

The measurement of bromide ion in the presence of other halide such as chloride is not a simple task. Ion Chromatography, titrimetric methods and ion selective probes can be used under certain test conditions. However, all of these methods are best suited for skilled laboratory technicians in a laboratory environment.

At aquatic facilities, it is common for maintenance workers or lifeguards to perform the water testing.

The use of ion chromatography is expensive and not practical for daily testing at an aquatic facility.

Furthermore, residential swimming pools typically use cyanurate based chlorine in the form of slow dissolving pucks (i.e. trichloroisocyanuric acid) or as a fast dissolving granular (sodium dichloroisocyanurate) products. The buildup of cyanurate causes over-stabilization of the chlorine thereby compromising the chlorine programs ability to control bacteria (coliform) and algae.

Addition of a bromide ion donor (i.e. sodium bromide) converts the treatment program into a free bromine treatment program which is not prone to over-stabilization from cyanurates. However, bromide ion concentrations must be sustained to a sufficient level to maintain microbiological efficacy for the bromine treatment program.

An easy to use method for determining the relative concentration of bromide ions is needed to ensure reliable and reproducible application of bromine based biocide.

SUMMARY OF THE INVENTION

The disclosed invention comprises a method for determining and controlling the relative concentration of at least bromide ions in an aqueous system of an aquatic facility (i.e. swimming pool) used for the production of free bromine.

Disclosed is a method for determining the relative bromide ion concentration in an aqueous system of an aquatic facility used for the production of free bromine, the method comprising: a composition comprising a bromide donor and a tracer, the composition is applied to the aqueous system to sustain a bromide ion concentration ranging from 2 ppm to 5000 ppm, more preferred from 4 to 500 ppm and most preferred from 5 to 100 ppm; the tracer is measured to determine the relative concentration of bromide ion, and the bromide ion concentration is maintained by adding additional composition to ensure sufficient free bromine can be produced to provide microbiological efficacy.

BRIEF DESCRIPTION OF THE DRAWING

FIG. 2 illustrates the stabilization of bromide ions and bromine's oxyhalogen surrogates (i.e. free bromine) by dialkylhydantoin in the presence of sunlight (UV).

FIG. 3 illustrates the improvement in chlorine dioxide generation when bromide ion is added to the aqueous system compared to free chlorine at near neutral pH.

FIG. 4 illustrates the microbiological efficacy of the cyclic process on inactivating *Cryptosporidium parvum* at two different chlorite concentrations using bromide ions activated by free chlorine at near neutral pH. The water chemistry and conditions applied in the test were consistent with water chemistry parameters used in aqueous systems at aquatic facilities. The data illustrates the microbiological efficacy of the cyclic process in achieving a 3-log and 4-log inactivation of *Cryptosporidium parvum*.

DETAILED DESCRIPTION OF THE INVENTION

Figure 1:
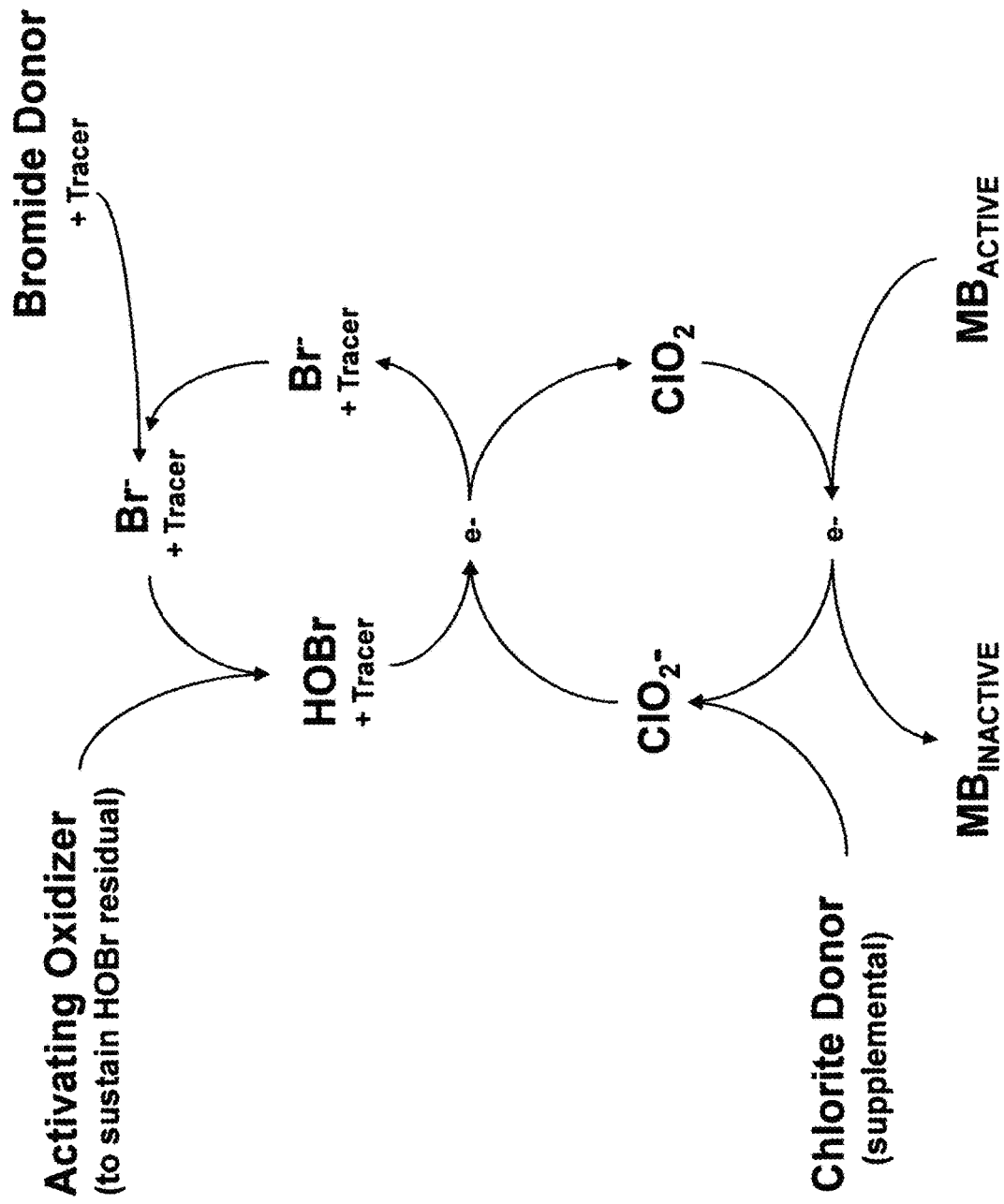
FIG. 1 illustrates the cyclic process where the bromide donor, bromide anion (Br—) and oxyhalogen surrogates (i.e. HOBr) of bromine are traced with an oxidizer inert tracer throughout the cyclic process.

Various compositions and methods of the invention are described below. Although particular compositions and methods are exemplified herein, it is understood that any of a number of alternative compositions and methods are applicable and suitable for use in practicing the invention.

The practice of the present invention will employ, unless otherwise indicated, conventional techniques of water chemistry, which are known to those of skill in the art. Such techniques are explained fully in the literature.

Definitions

As used herein, "molybdate donor" comprises a compound that when dissolved in water release molybdate having the general formula $MoO_4^{2-}$. Non-limiting examples of molybdate donors include sodium molybdate, potassium molybdate, lithium molybdate and the like.

As used herein, the term "tracer" describes a chemical compound that is inert to the oxidizers used to treat the aqueous system of the aquatic facility and is combined with at least the bromide donor to form a composition. The composition can be in the form of a solid or liquid. The tracer can be detected and quantitatively measured.

As used herein, the term "oxidizing activator" is used with reference to an oxidizer selected from at least one of: free chlorine, peroxymonosulfate, alkali metal salts or ammonium salts of persulfates and electrolysis; wherein when the activating oxidizer is introduced to the aqueous system comprising bromide anions, the activating oxidizer reacts with bromide anion resulting in the formation of free bromine.

As used herein, the term "free chlorine" is used with reference to a chlorine source that hydrolyses in the aqueous system to produce at least some portion of hypochlorous acid.

As used herein, the term "free bromine" is used with reference to the formation or presence of hypobromous acid and possibly some portion of hypobromite ions.

As used herein, the term "relative bromide ion concentration" is used with reference to the approximate concentration of bromide ion. The tracer is combined with the bromide donor at a known ratio. Since the tracer is not directly combined with the bromide ion and simply shadows the bromide ion, and understanding some bromide ion has been converted to free bromine there is going to be some variance between the actual concentration of bromide ion and measured tracer. For this reason, the measurement of tracer provides for the "relative bromide ion concentration".

As used herein, the term "near neutral pH" is used with reference the pH of the aqueous system of between about 6.0 and 8.5. However, more preferred is a pH of about 6.8 to 8.0 where the ratio of hypobromous acid as compared to hypobromite ions is low, and the potential for formation of bromine gas is reduced.

As used herein, the term "inactivation" is used with reference to the ability to deactivate, kill, or destroy microbiological organisms.

As used herein, the term "microbiological organisms" is used with reference to all forms of microbiological life forms including: parasites, bacteria, viruses, algae, fungus, and organisms encased in biofilms.

As used herein, the term "free halogen donor" is used with reference to a halogen source which acts as an active oxidizer when dissolved in water. Chlorine based free halogen donors form at least one of $Cl_2$, $HOCl$, and $OCl^-$ (also referred to as free chlorine) when added to water, whereby the species formed is pH dependent. Bromine based free halogen donors form at least one of $Br_2$, $HOBr$, and $OBr^-$ (also referred to as free bromine), again the species being pH dependent.

As used herein, the term "peroxymonosulfate" encompasses the various species of the peracid chemistry and its various salts, whereby depending on the pH of the solution in which the peroxymonosulfate is added, the following species and combinations result: $H_2SO_5$ (Caro's acid), $HSO_5^-$, $SO_5^=$.

As used herein, the term "aquatic facility" is used with reference to all structural components and equipment comprising an aqueous system used by humans for exercise, sports and/or recreation. Examples of aquatic facilities include but are not limited to: water parks, theme parks, swimming pools, spas, residential swimming pools, mammal habits at zoos, therapy pools, hot tubs and the like.

As used herein, the term "aqueous system" describes that portion of the aquatic facility comprising water (also referred to as the "aqueous solution").

As used herein, the term "recreational water" is defined as the water contained in the swimming pool, hot tub, feature pool, water park etc. used by people using the aquatic facility.

As used herein, the term "cyclic process" relates to the recycling of substantially inert anions comprising bromide and chlorite into their oxyhalogen surrogates, exemplified by hypobromous acid and chlorine dioxide respectfully followed by reduction back to their respective anions, and where the process is repeated.

As used herein, the term "chlorite anion donor" is a compound that comprises an alkali metal salt comprising chlorite anions $ClO_2^-$, chlorine dioxide, or any convenient direct or indirect source of chlorite anions. For example, chlorine dioxide can indirectly produce chlorite due to reduction in an aqueous system. Sodium chlorite directly supplies chlorite anions. Regardless of whether the chlorite anion is provided by a direct or indirect chlorite anion donor, any chlorite anions in the aqueous system implementing the disclosed cyclic process of the invention will be regenerated to chlorine dioxide in the disclosed cyclic process.

As used herein, the term "chlorite anion" is comprises chlorite having the general formula $ClO_2^-$.

As used herein, the term "recycled" also "recycling" means at least some portion of the recovered bromide anions and chlorite anions are regenerated to their respective oxyhalogen compounds, followed by reduction back to their respective anions, and where the process is repeated.

As used herein, the term "*Cryptosporidium*" is used to represent any form of parasitic microbiological organism from the family of *Cryptosporidium*. An example of *Cryptosporidium* is *Cryptosporidium parvum* (also referred to as *C. parvum*, *C. parvum* and *Cryptosporidium parvum*). Other examples of *Cryptosporidium* include but are not limited to: *C. hominis*, *C. canis*, *C. felis*, *C. meleagridis*, and *C. muris*. It is to be noted that inclusion or exclusion of italic characters or print when referring to *Cryptosporidium* or any of its many variants does not in any way detract from its intended descriptive meaning.

As used herein, "microbiological efficacy" is used to describe the treatment program's ability to inactivate microbiological organisms. Using the cyclic process, the microbiological efficacy is defined as the ability to maintain the aqueous system free of coliform bacteria and/or achieve at least a 3-log inactivation of *Cryptosporidium*, more preferred achieving at least a 4-log inactivation of *Cryptosporidium*. When describing the free bromine treated aqueous system, microbiological efficacy is defined by the ability to maintain the aqueous system free of coliform bacteria.

In one embodiment the invention is a method for determining the relative bromide ion concentration in an aqueous system of an aquatic facility using the cyclic process, the method comprising: a composition comprising a bromide donor and a tracer, the composition is applied to the aqueous system to maintain a bromide ion concentration ranging from 2 ppm to 5000 ppm; the tracer is measured to determine the relative concentration of bromide ion, and the bromide ion concentration is maintained by adding additional composition to ensure the cyclic process and subsequent microbiological efficacy is achieved.

In another embodiment disclosed is a method for determining the relative bromide ion concentration in an aqueous system of an aquatic facility using free bromine resulting from the reaction between an oxidizing activator and bromide ions, the method comprising: a composition comprising a bromide donor and a tracer, the composition is applied to the aqueous system to maintain a bromide ion concentration ranging from 2 ppm to 5000 ppm; the tracer is measured to determine the relative concentration of bromide ion, and the bromide ion concentration is maintained by adding additional composition to ensure sufficient free bromine and subsequent microbiological efficacy is achieved.

In another embodiment of the invention, the composition comprising a bromide donor and a tracer further comprises dialkylhydantoin.

The microbiological efficacy for the cyclic process is determined by achieving maintaining the aqueous system free of coliform bacteria, and/or at least a 3-log inactivation of *Cryptosporidium*, more preferred achieving at least a 4-log inactivation of *Cryptosporidium*.

The microbiological efficacy for a free bromine treated aqueous system is maintaining the aqueous system free of coliform bacteria.

Coliform bacteria are defined as rod-shaped Gram-negative non-spore forming and motile or non-motile bacteria which can ferment lactose with the production of acid and gas when incubated at 35-37° C. They are a commonly used indicator of sanitary quality of foods and water. Coliforms can be found in the aquatic environment, in soil and on vegetation; they are universally present in large numbers in the feces of warm-blooded animals. While coliforms themselves are not normally causes of serious illness, they are easy to culture, and their presence is used to indicate that other pathogenic organisms of fecal origin may be present. Such pathogens include disease-causing bacteria, viruses, or protozoa and many multicellular parasites. Coliform procedures are performed in aerobic or anaerobic conditions. Typical genera include: *Citrobacter*, *Enterobacter*, *Hafnia*, *Klebsiella*, *Escherichia*

*Escherichia coli* (*E. coli*) can be distinguished from most other coliforms by its ability to ferment lactose at 44° C. in the fecal coliform test.

The tracer should be inert to the oxidizers used to treat the aqueous system of the aquatic facility. Furthermore the tracer should be non-toxic and environmentally benign.

Examples of suitable tracers include but are not limited to molybdate donor(s) and cyanurate(s). The preferred tracer is a molybdate donor.

Molybdate (i.e. sodium molybdate) is an oxoanion of molybdenum in its highest oxidation state of 6. This makes molybdate ideal for use in applications such as the cyclic process as it is stable from further oxidation and precipitation.

Molybdate is easily measured using colorimetric methods like those used at aquatic facilities. Companies such as PalinTest® and Hach® provide easy to use test kits for determining low level molybdate (i.e. 0.02 ppm) concentrations without interference from other metals at typical concentrations found in aquatic facilities.

Sodium molybdate ($Na_2MoO_4$) is one non-limiting example of preferred molybdate donor suitable for use as a tracer. Other non-limiting examples include: lithium, potassium and ammonium molybdates to name a few.

The concentration of molybdate can range from 0.02-2 ppm reported as molybdate ($MoO_4^{2-}$). The measured result of the test can also be reported as molybdenum (Mo) by multiplying the molybdate concentration by a factor of 0.6. For example, a molybdate concentration of 0.02 ppm (reported $MoO_4^{2-}$) is equivalent to 0.012 ppm (reported as Mo).

The tracer is combined with the bromide donor by mixing the tracer and bromide donor together at a known ratio to form a composition. The composition can be in the form of a solid or liquid.

The solid composition can be further formed into any number of non-limiting geometric shapes such as a tablet, pellet or puck.

The weight percent ratio of tracer to bromide donor can vary based on which tracer and donor are used. For example, sodium molybdate has a different formula weight than potassium molybdate and therefore to obtain the same molybdate concentration, more potassium molybdate is required in the composition to compensate for the higher formula weight.

The composition can further include other additives that can be monitored for their relative concentration by measuring the tracer. For example, dialkylhydantoins are effective UV stabilizers of free bromine. The UV stabilization of free bromine inhibits the formation to bromate when exposed to sunlight (UV). Non-limiting examples of suitable dialkylhydantoins include: 5,5-dimethylhydantoin and 5-ethyl-5-methylhydantoin.

The tracer concentration in the aqueous system ranges from 0.02 to 2.0 ppm reported as molybdate ($MoO_4^{2-}$). Preferably the tracer concentration ranges from 0.05 to 1.0 ppm as molybdate, and most preferred from 0.10 to 0.80 ppm as molybdate.

The bromide ion concentration ranges from 2 to 5000 ppm as bromide ($Br^-$). The preferred bromide concentration ranges from 4 to 500 ppm as bromide and the most preferred bromide concentration ranges from 5 to 100 ppm as bromide.

The composition comprising a molybdate donor and bromide donor has a weight percent ratio of molybdate ($MoO_4^{2-}$) to bromide ($Br^-$) ranging from 1:25000 to 1:5000, more preferably 1:5000 to 1:1000, and most preferred between 1:1000 and 1:10.

The oxidizer inert tracer shadows the bromide ions in the aqueous system. When water is lost due to filter backwash, splashing or draining, both the tracer and bromide ion concentration decrease. When the tracer concentration reaches or drops below the desired minimum concentration, additional composition can be applied to the aqueous system to sustain the bromide ion concentration.

EXAMPLE

Sodium molybdate was obtained from Sigma Aldrich, sodium bromide was obtained from Albemarle Corporation and 25 wt % active sodium chlorite was obtained from OxyChem Corporation.

An 18'×33' oval shaped pool with approximately 4 feet of water was treated with a composition comprising 14 g of $Na_2MoO_4$ and 2400 g of NaBr. The composition was produced by combining both ingredients and mixing. The pool was treated with trichloroisocyanuric acid to sustain between 2 mg/l to 3 mg/l chlorine (reported as $Cl_2$).

The composition was added directly to the pool water and allowed to dissolve and dissipate in the pool water for several hours. A sample of pool water was collected and tested using a Hach® DR2800 spectrophotometer using low range molybdenum reagents. The pH was measured at 7.57.

The molybdenum (as Mo) measured 0.09 mg/l. The molybdate (as $MoO_4^{2-}$) concentration was obtained by multiplying the molybdenum concentration by 1.67 resulting in a molybdate concentration of 0.15 mg/l. Based on the amount of sodium molybdate added to the pool and the result of the molybdate test, the pool volume was calculated to be 72,482 liters or 19,150 gallons.

Based on the pool volume, the bromide ion (as $Br^-$) concentration is calculated to be approximately 25 mg/l (as $Br^-$).

During evening hours (after dusk), 490 g of 25 wt % active sodium chlorite was added to the pool. The treatment was allowed to circulate for approximately 1 hour. A sample was collected and a lissamine green test was performed using a PalinTest® spectrophotometer with low range lissamine green reagent. The lissamine green treated sample was allowed to react for 20 minutes before measuring the chlorine dioxide concentration. The result of the lissamine green test was 0.25 mg/l as $ClO_2$.

The example illustrates that the method and composition of the disclosed invention for monitoring and controlling the relative concentration of bromide ion used in the cyclic process is effective.

It is claimed:

1. A method for determining the relative bromide ion concentration in an aqueous system of an aquatic facility using a cyclic process, the method comprising:
   the cyclic process comprising activating bromide ions with an oxidant to produce free bromine, the free bromine oxidizes chlorite ions to produce chlorine dioxide, and reducing at least some free bromine back to bromide ions,
   applying a composition comprising a bromide donor and a tracer; the composition is applied to the aqueous system to maintain a bromide ion concentration ranging from 2 ppm to 5000 ppm;
   measuring the tracer to determine the relative concentration of bromide ion, and
   maintaining the bromide ion concentration by adding additional composition to ensure the cyclic process and subsequent microbiological efficacy is achieved.

2. The method in accordance with claim 1, wherein the tracer comprises a molybdate donor.

3. The method in accordance with claim 2, wherein the molybdate donor comprises sodium molybdate.

4. The method in accordance with claim 2, wherein the concentration of molybdate measured in the aqueous system is sustained between 0.02 ppm to 2.0 ppm.

5. The method in accordance with claim 4, wherein the concentration of molybdate measured in the aqueous system is sustained between 0.05 ppm to 1.0 ppm.

6. The method in accordance with claim 5, wherein the concentration of molybdate measured in the aqueous system is sustained between 0.10 ppm to 0.80 ppm.

7. The method in accordance with claim 1, wherein the bromide ion concentration ranges from 4 ppm to 500 ppm.

8. The method in accordance with claim 7, wherein the bromide ion concentration ranges from 5 ppm to 100 ppm.

9. The method of claim 1, the composition further comprising dialkylhydantoin.

10. The composition in accordance with claim 9, wherein the dialkylhydantoin comprises 5,5-dimethylhydantoin.

11. The composition in accordance with claim 9, wherein the dialkylhydantoin comprises 5-ethyl-5-methylhydantoin.

12. The method in accordance with claim 1, wherein the microbiological efficacy comprises achieving at least a 3-log inactivation of *Cryptosporidium*.

13. The method in accordance with claim 12, wherein the microbiological efficacy comprises achieving at least a 4-log inactivation of *Cryptosporidium*.

14. The method in accordance with claim 1, wherein the microbiological efficacy comprises maintaining the aqueous system free of coliform bacteria.

15. A method for determining the relative bromide ion concentration in an aqueous system of an aquatic facility using free bromine resulting from the reaction between an oxidizing activator and bromide ions, the method comprising:
   applying a composition comprising a bromide donor and a tracer; the composition is applied to the aqueous system to maintain a bromide ion concentration ranging from 2 ppm to 5000 ppm;

measuring the tracer to determine the relative concentration of bromide ions, and maintaining the bromide ion concentration by adding additional composition to ensure sufficient free bromine and subsequent microbiological efficacy is achieved.

16. The method in accordance with claim 15, wherein the tracer is molybdate donor.

17. The method in accordance with claim 16, wherein the molybdate donor comprises sodium molybdate.

18. The method in accordance with claim 16, wherein the concentration of molybdate measured in the aqueous system is sustained between 0.02 ppm to 2.0 ppm.

19. The method in accordance with claim 18, wherein the concentration of molybdate measured in the aqueous system is sustained between 0.05 ppm to 1.0 ppm.

20. The method in accordance with claim 19, wherein the concentration of molybdate measured in the aqueous system is sustained between 0.10 ppm to 0.80 ppm.

21. The method in accordance with claim 15, wherein the bromide ion concentration ranges from 4 ppm to 500 ppm.

22. The method in accordance with claim 21, wherein the bromide ion concentration ranges from 5 ppm to 100 ppm.

23. The method of claim 15, the composition further comprising dialkylhydantoin.

24. The method in accordance with claim 23, wherein the dialkylhydantoin comprises 5,5-dimethylhydantoin.

25. The method in accordance with claim 23, wherein the dialkylhydantoin comprises 5-ethyl-5-methylhydantoin.

26. The method in accordance with claim 15, wherein the microbiological efficacy comprises maintaining the aqueous system free of coliform bacteria.

* * * * *